US011331006B2

(12) United States Patent
Gingrich et al.

(10) Patent No.: US 11,331,006 B2
(45) Date of Patent: May 17, 2022

(54) SYSTEM AND METHOD FOR HUMAN MOTION DETECTION AND TRACKING

(71) Applicant: Physmodo, Inc., Dallas, TX (US)

(72) Inventors: Nathanael Lloyd Gingrich, Dallas, TX (US); Gregory Murray Smith, Lewisville, TX (US)

(73) Assignee: Physmodo, Inc., Dallas, TX (US)

( * ) Notice: Subject to any disclaimer, the term of this patent is extended or adjusted under 35 U.S.C. 154(b) by 0 days.

(21) Appl. No.: 17/362,299

(22) Filed: Jun. 29, 2021

(65) Prior Publication Data

US 2021/0338110 A1    Nov. 4, 2021

Related U.S. Application Data

(63) Continuation-in-part of application No. 17/260,477, filed as application No. PCT/US2020/021262 on Mar. 5, 2020, now Pat. No. 11,103,748.

(Continued)

(51) Int. Cl.
*A61B 5/11*    (2006.01)
*A61B 5/00*    (2006.01)

(52) U.S. Cl.
CPC .......... *A61B 5/1114* (2013.01); *A61B 5/0064* (2013.01); *A61B 5/0077* (2013.01);
(Continued)

(58) Field of Classification Search
None
See application file for complete search history.

(56) References Cited

U.S. PATENT DOCUMENTS

| 4,836,670 A | 6/1989 | Hutchinson |
| 6,269,172 B1 * | 7/2001 | Rehg ............. G06K 9/00369 342/1 |

(Continued)

FOREIGN PATENT DOCUMENTS

| CN | 102402288 | 4/2012 |
| CN | 105069413 | 11/2015 |
| WO | 2020181136 | 9/2020 |

OTHER PUBLICATIONS

Longbo Kong et al. "A Hybrid Framework for Automatic Joint Detection of Human Poses in Depth Frames," Patterns Recognition vol. 77. May 2018, pp. 216-225.

(Continued)

*Primary Examiner* — Peet Dhillon
(74) *Attorney, Agent, or Firm* — Scott Griggs; Griggs Bergen LLP

(57) ABSTRACT

A system and method for human motion detection and tracking are disclosed. In one embodiment, a smart device having an optical sensing instrument monitors a stage. Memory is accessible to a processor and communicatively coupled to the optical sensing instrument. The system captures an image frame from the optical sensing instrument. The image frame is then converted into a designated image frame format, which is provided to a pose estimator. A two-dimensional dataset is received from the pose estimator. The system then converts, using inverse kinematics, the two-dimensional dataset into a three-dimensional dataset, which includes time-independent static joint positions, and then calculates, using the three-dimensional dataset, the position of each of the respective plurality of body parts in the image frame.

20 Claims, 8 Drawing Sheets

Related U.S. Application Data

(60) Provisional application No. 63/155,653, filed on Mar. 2, 2021, provisional application No. 62/814,147, filed on Mar. 5, 2019.

(52) U.S. Cl.
CPC ............ *A61B 5/7264* (2013.01); *A61B 5/742* (2013.01); *A61B 5/7475* (2013.01)

(56) References Cited

U.S. PATENT DOCUMENTS

| | | | |
|---|---|---|---|
| 6,323,846 B1 | 11/2001 | Westerman et al. | |
| 6,351,273 B1 | 2/2002 | Lemelson et al. | |
| 7,070,571 B2 | 7/2006 | Kramer et al. | |
| 7,561,143 B1 | 7/2009 | Milekic | |
| 7,883,415 B2 | 2/2011 | Larsen et al. | |
| 8,253,746 B2 | 8/2012 | Geisner et al. | |
| 8,502,864 B1 | 8/2013 | Watkins | |
| 8,593,375 B2 | 11/2013 | Maltz | |
| 8,823,642 B2 | 9/2014 | Valik et al. | |
| 8,876,739 B2 | 11/2014 | Salarian et al. | |
| 8,896,522 B2 | 11/2014 | Valik et al. | |
| 9,149,222 B1 | 10/2015 | Zets et al. | |
| 2002/0135581 A1* | 9/2002 | Russell | G06T 7/11 345/474 |
| 2003/0151592 A1 | 8/2003 | Ritter | |
| 2004/0141635 A1 | 7/2004 | Liang et al. | |
| 2004/0227992 A1 | 11/2004 | Putilin et al. | |
| 2007/0139370 A1 | 6/2007 | Lu et al. | |
| 2007/0139443 A1 | 6/2007 | Marks et al. | |
| 2008/0212836 A1 | 9/2008 | Fujimura et al. | |
| 2008/0221487 A1 | 9/2008 | Zohar et al. | |
| 2009/0172606 A1 | 7/2009 | Dunn et al. | |
| 2009/0268945 A1 | 10/2009 | Wilson et al. | |
| 2009/0296992 A1 | 12/2009 | Liang et al. | |
| 2010/0033427 A1 | 2/2010 | Marks et al. | |
| 2010/0079413 A1 | 4/2010 | Kawashima et al. | |
| 2010/0080464 A1 | 4/2010 | Sawai et al. | |
| 2010/0277489 A1 | 11/2010 | Geisner et al. | |
| 2011/0090149 A1 | 4/2011 | Larsen et al. | |
| 2011/0092860 A1 | 4/2011 | Kramer et al. | |
| 2011/0102570 A1 | 5/2011 | Wilf et al. | |
| 2011/0154266 A1 | 6/2011 | Friend et al. | |
| 2011/0261178 A1 | 10/2011 | Lo et al. | |
| 2011/0296333 A1 | 12/2011 | Bateman et al. | |
| 2011/0298827 A1* | 12/2011 | Perez | G06K 9/00355 345/647 |
| 2012/0056982 A1 | 3/2012 | Katz et al. | |
| 2012/0173067 A1 | 7/2012 | Szczerba et al. | |
| 2012/0200600 A1 | 8/2012 | Demaine | |
| 2012/0249590 A1 | 10/2012 | Maciocci et al. | |
| 2012/0249591 A1 | 10/2012 | Maciocci et al. | |
| 2012/0249741 A1 | 10/2012 | Maciocci et al. | |
| 2013/0010071 A1 | 1/2013 | Valik et al. | |
| 2013/0010207 A1 | 1/2013 | Valik et al. | |
| 2013/0223707 A1 | 8/2013 | Stephenson | |
| 2013/0268205 A1 | 10/2013 | Aragones et al. | |
| 2014/0009384 A1 | 1/2014 | Valik et al. | |
| 2014/0254883 A1 | 9/2014 | Kim et al. | |
| 2014/0276095 A1 | 9/2014 | Griggs et al. | |
| 2015/0070274 A1 | 3/2015 | Morozov | |
| 2016/0247017 A1 | 8/2016 | Sareen et al. | |
| 2016/0346601 A1 | 12/2016 | Marcandelli et al. | |
| 2017/0086712 A1 | 3/2017 | Mauro et al. | |
| 2018/0164947 A1 | 6/2018 | Mizuhashi et al. | |
| 2018/0189550 A1 | 7/2018 | McCombe et al. | |
| 2019/0038181 A1* | 2/2019 | Domeika | A61B 5/7267 |
| 2020/0256669 A1 | 8/2020 | Roth et al. | |

OTHER PUBLICATIONS

Ankur Agarwal et al. "Recovering 3D human pose from monocular images". IEEE Transactions on Pattern Analysis and Machine Intelligence, Institute of Electrical and Electronics Engineers, 2006, 28 (1), pp. 44-58. ff10.1109/TPAMI.2006.21ff. ffinria-00548619.

Alireza Shafaei et al. "Real-Time Human Motion Capture with Multiple Depth Cameras," 2016 13th Conference on Computer and Robot Vision (CRV), Victoria, BC, 2016, pp. 24-31, doi: 10.1109/CRV.2016.25.

PCT/US20/21262 Notification of Transmittal of the International Search Report and the Written Opinion of the International Searching Authority, or the Declaration filed Mar. 5, 2020.

PCT/US18/12080 Notification of Transmittal of the International Search Report and the Written Opinion of the International Searching Authority, or the Declaration filed Jan 2, 2018.

"Squat with Arm raise," YouTube Video Captured at the 5th, 6th, and 8th Second out of 15 Seconds, published on Apr. 28, 2016, URL https://www.youtube.com/watch?v=bHSUwyX-2JQ; Downloaded on Oct. 11, 2018.

\* cited by examiner

SYSTEM AND METHOD FOR HUMAN MOTION DETECTION AND TRACKING

PRIORITY STATEMENT & CROSS-REFERENCE TO RELATED APPLICATIONS

This application claims priority from U.S. Patent Application No. 63/155,653, entitled "System and Method for Human Motion Detection and Tracking" and filed on Mar. 2, 2021, in the names of Nathanael Lloyd Gingrich et al.; which is hereby incorporated by reference, in entirety, for all purposes. This application is also a continuation-in-part of U.S. patent application Ser. No. 17/260,477, entitled "System and Method for Human Motion Detection and Tracking" and filed on Jan. 14, 2021, in the name of Longbo Kong; which is a 371 national entry application of PCT/US20/21262 entitled "System and Method for Human Motion Detection and Tracking" and filed on Mar. 5, 2020, in the name of Longbo Kong; which claims priority from U.S. Patent Application No. 62/814,147, entitled "System and Method for Human Motion Detection and Tracking" and filed on Mar. 5, 2019, in the name of Longbo Kong; all of which are hereby incorporated by reference, in entirety, for all purposes.

TECHNICAL FIELD OF THE INVENTION

The present disclosure relates, in general, to biomechanical evaluations and assessments, which are commonly referred to as range of motion assessments, and more particularly, to automating a biomechanical evaluation process, including a range of motion assessment, and providing recommended exercises to improve physiological inefficiencies of a user.

BACKGROUND OF THE INVENTION

Human beings have regularly undergone physical examinations by professionals to assess and diagnose their health issues. Healthcare history has been predominantly reactive to an adverse disease, injury, condition or symptom. Increasingly, in modern times, with more access to information, a preventative approach to healthcare has been gaining greater acceptance. Musculoskeletal health overwhelmingly represents the largest health care cost. Generally speaking, a musculoskeletal system of a person may include a system of muscles, tendons and ligaments, bones and joints, and associated tissues that move the body and help maintain the physical structure and form. Health of a person's musculoskeletal system may be defined as the absence of disease or illness within all of the parts of this system. When pain arises in the muscles, bones, or other tissues, it may be a result of either a sudden incident (e.g., acute pain) or an ongoing condition (e.g., chronic pain). A healthy musculoskeletal system of a person is crucial to health in other body systems, and for overall happiness and quality of life. Musculoskeletal analysis, or the ability to move within certain ranges (e.g., joint movement) freely and with no pain, is therefore receiving greater attention. However, musculoskeletal analysis has historically been a subjective science, open to interpretation of the healthcare professional or the person seeking care.

In 1995, after years of research, two movement specialists, Gray Cook and Lee Burton, attempted to improve communication and develop a tool to improve objectivity and increase collaboration efforts in the evaluation of musculoskeletal health. Their system, the Functional Movement Screen (FMS), is a series of seven (7) different movement types, measured and graded on a scale of 0-3. While their approach did find some success in bringing about a more unified approach to movement assessments, the subjectivity, time restraint and reliance on a trained and accredited professional to perform the evaluation limited its adoption. Accordingly, there is a need for improved systems and methods for measuring and analyzing physiological deficiency of a person and providing corrective recommended exercises while minimizing the subjectivity during a musculoskeletal analysis.

SUMMARY OF THE INVENTION

It would be advantageous to achieve systems and methods that would improve upon existing limitations in functionality with respect to measuring and analyzing physiological deficiency of a person. It would also be desirable to enable a computer-based electronics and software solution that would provide enhanced goniometry serving as a basis for furnishing corrective recommended exercises while minimizing the subjectivity during a musculoskeletal analysis. To better address one or more of these concerns, a system and method for human motion detection and tracking are disclosed. In one embodiment, a smart device having an optical sensing instrument monitors a stage. A memory is accessible to a processor and communicatively coupled to the optical sensing instrument. The system captures an image frame from the optical sensing instrument. The image frame is then converted into a designated image frame format, which is provided to a pose estimator. A two-dimensional dataset is received from the pose estimator. The system then converts, using inverse kinematics, the two-dimensional dataset into a three-dimensional dataset, which includes time-independent static joint positions, and then calculates, using the three-dimensional dataset, the position of each of the respective plurality of body parts in the image frame. These and other aspects of the invention will be apparent from and elucidated with reference to the embodiments described hereinafter.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which.

DETAILED DESCRIPTION OF THE INVENTION

While the making and using of various embodiments of the present invention are discussed in detail below, it should be appreciated that the present invention provides many applicable inventive concepts, which can be embodied in a wide variety of specific contexts. The specific embodiments discussed herein are merely illustrative of specific ways to make and use the invention, and do not delimit the scope of the present invention.

Figure 1A:
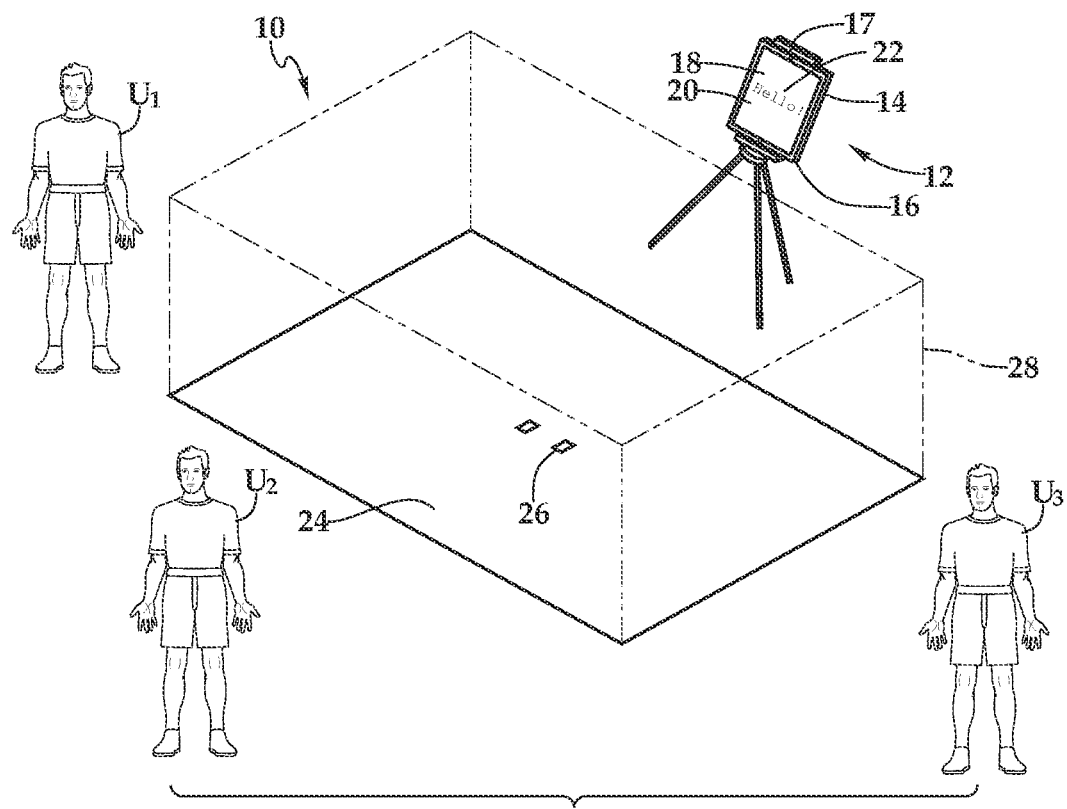
FIG. 1A is a schematic diagram depicting one embodiment of a system and method for human motion detection tracking for use, for example, with an integrated goniometry system for measuring and analyzing physiological deficiency of a person, such as a user, and providing corrective recommended exercises according to an exemplary aspect of the teachings presented herein.

Referring initially to FIG. 1A, therein is depicted one embodiment of a system for human motion detection and tracking that may be incorporated into an integrated goniometry system, for example, for performing automated biomechanical movement assessments, which is schematically illustrated and designated 10. As shown, the integrated goniometry system 10 includes a smart device 12, which may function as an integrated goniometer, having a housing 14 securing an optical sensing instrument 16 and a display 18. The display 18 includes an interactive portal 20 which provides prompts, such as an invitation prompt 22, which may greet a crowd of potential users $U_1$, $U_2$, and $U_3$ and invite a user to enter a stage 24, which may include markers 26 for foot placement of the user standing at the markers 26 to utilize the integrated goniometry system 10. The stage 24 may be a virtual volumetric area 28, such as a rectangular or cubic area, that is compatible with human exercise positions and movement. The display 18 faces the stage 24 and the optical sensing instrument 16 monitors the stage 24. A webcam may be included in some embodiments. It should be appreciated that the location of the optical sensing instrument 16 and the webcam 17 may vary with the housing 14. Moreover, the number of optical sensing instruments used may vary also. Multiple optical sensing instruments or an array thereof may be employed. It should be appreciated that the design and presentation of the smart device 12 may vary depending on application. By way of example, the smart device 12 and the housing 14 may be a device selected from the group consisting of, with or without tripods, smart phones, smart watches, smart wearables, and tablet computers, for example.

Figure 1B:
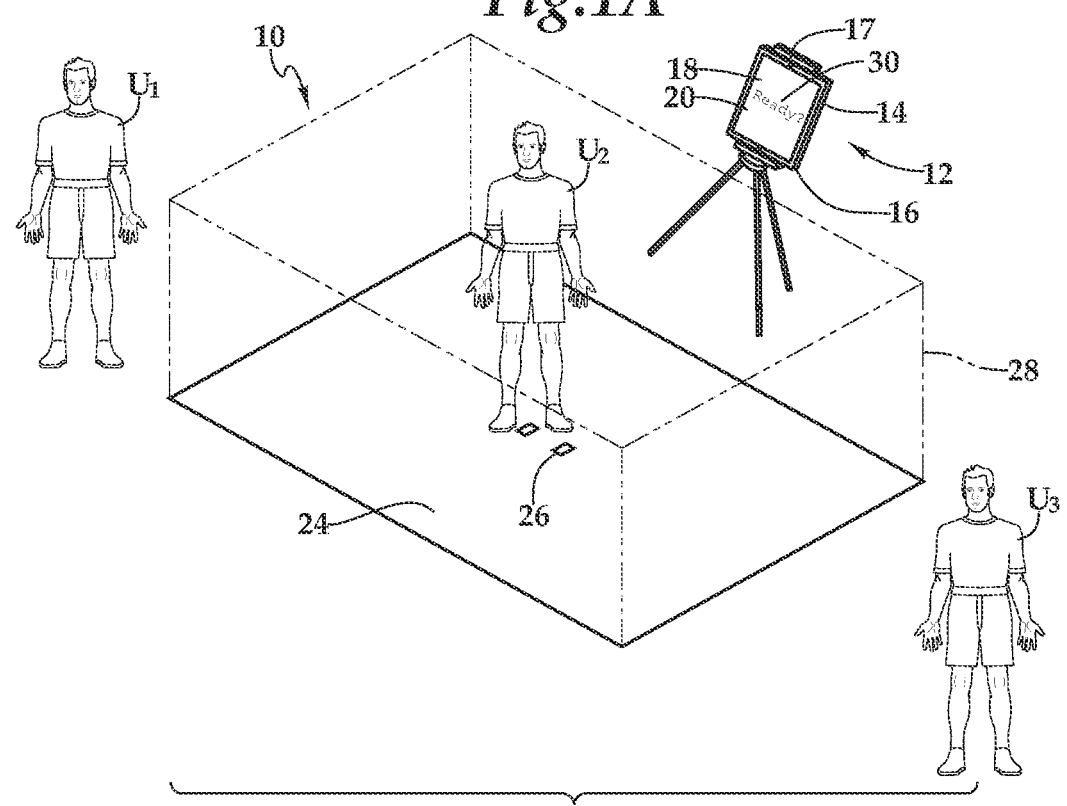
FIG. 1B is a schematic diagram depicting one embodiment of the system illustrated in FIG. 1A, wherein a user from a crowd has approached the system.

Referring now to FIG. 1B, the user, user $U_2$, has entered the stage 24 and the interactive portal 20 includes an exercise movement prompt 30 providing instructions for the user $U_2$ on the stage 24 to execute a set number of repetitions of an exercise movement, such as a squat or a bodyweight overhead squat, for example. In some implementations, the interactions with the user $U_2$ are contactless and wearableless. A series of prompts on the interactive portal 20 instruct the user $U_2$ while the optical sensing instrument 16 senses body point data of the user $U_2$ during each exercise movement. Based on the sensed body point data, a mobility score, an activation score, a posture score, a symmetry score, or any combination thereof, for example, may be calculated. A composite score may also be calculated. One or more of the calculated scores may provide the basis for the integrated goniometry system 10 determining an exercise recommendation. As mentioned, a series of prompts on the interactive portal instruct the user $U_2$ through repetitions of exercise movements while the optical sensing instrument 16 senses body point data of the user $U_2$. It should be appreciated that the smart device 12 may be supported by a server that provides various storage and support functionality to the smart device 12. Further, the integrated goniometry system 10 may be deployed such that the server is remotely located in a cloud C to service multiple sites with each site having a smart device.

Figure 2:
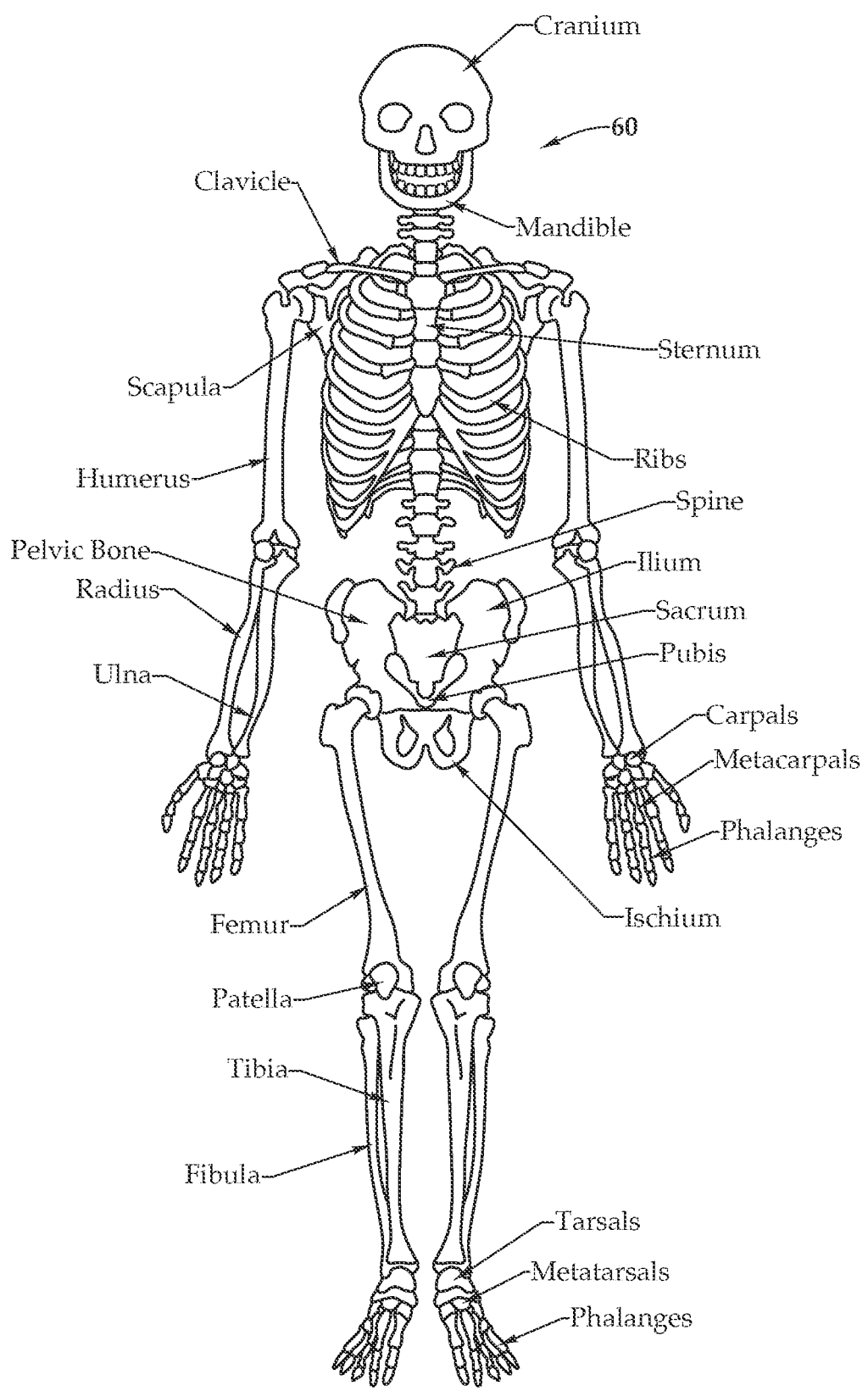
FIG. 2 is an illustration of a human skeleton.
Figure 3:
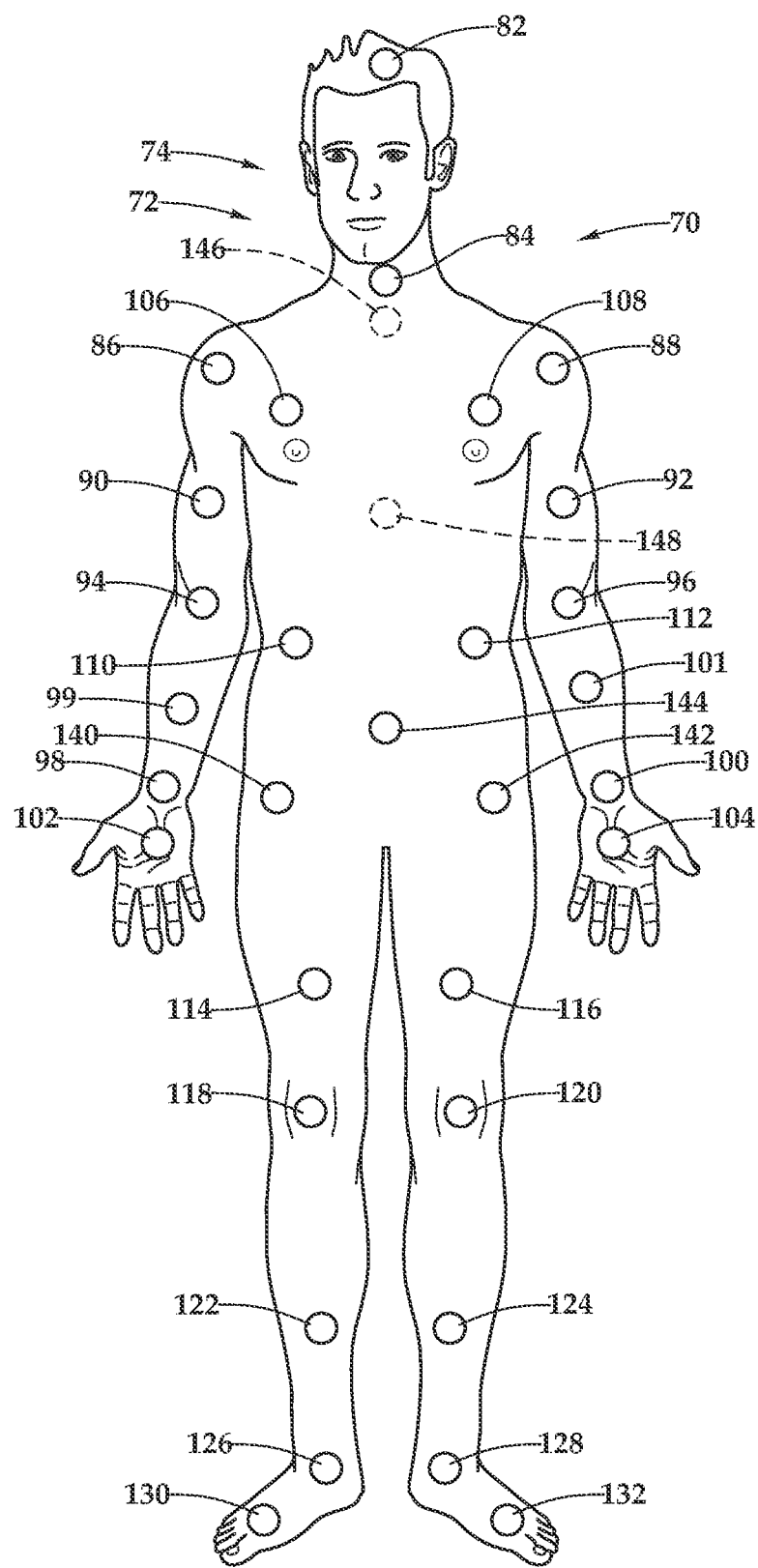
FIG. 3 is an illustration of one embodiment of body parts identified by the system.

Referring now to FIG. 2 and FIG. 3, respective embodiments of a human skeleton 60 and body parts identified by the integrated goniometry system 10 are depicted. Body part data 70 approximates certain locations and movements of the human body, represented by the human skeleton 60. More specifically, the body part data 70 is captured by the optical sensing instrument 16 and may include designated body part data 72 and synthetic body part data 74. By way of example and not by way of limitation, designated body part data 72 may include head data 82, neck data 84, right shoulder data 86, left shoulder data 88, right upper arm data 90, left upper arm data 92, right elbow data 94, left elbow data 96, right lower arm data 99, left lower arm data 101, right wrist data 98, left wrist data 100, right hand data 102, left hand data 104, right upper torso data 106, left upper torso data 108, right lower torso data 110, left lower torso data 112, upper right leg data 114, upper left leg data 116, right knee data 118, left knee data 120, right lower leg data 122, left lower leg data 124, right ankle data 126, left ankle data 128, right foot data 130, and left foot data 132. By way of example and not by way of limitation, synthetic body part data 74 may include right hip 140, left hip 142, waist 144, top of spine 146, and middle of spine 148. As will be appreciated, the synthetic body part data 74 may include data captured by the optical sensing instrument 16 that includes locations in the body in the rear of the person or data acquired through inference.

Figure 4:
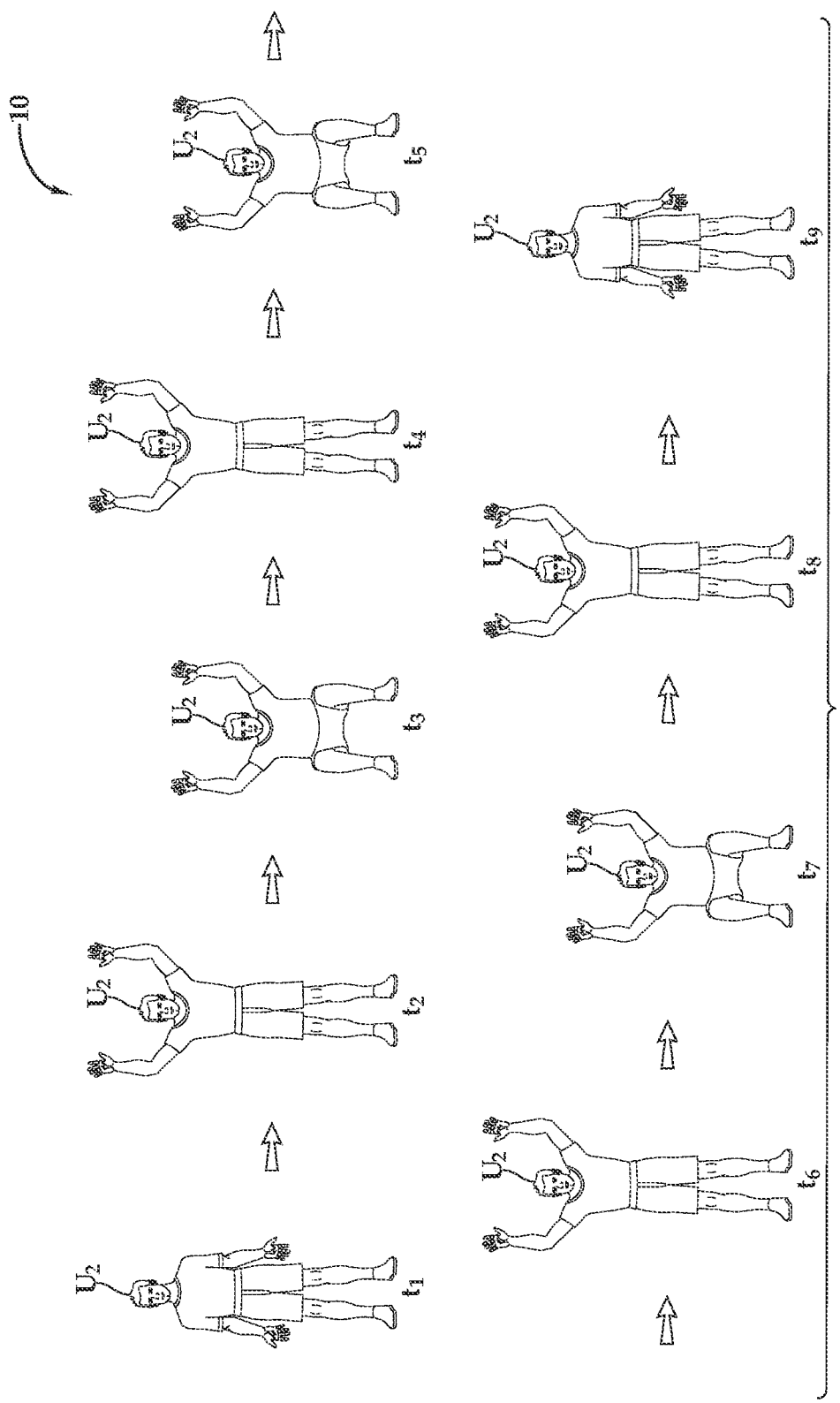
FIG. 4 is a diagram depicting one embodiment of a set number of repetitions which are monitored and captured by the system.

Referring now to FIG. 4, image frames associated with a set number of repetitions of an exercise movement by the user $U_2$ are monitored and captured by the integrated goniometry system 10. As shown, in the illustrated embodiment, the user $U_2$ executes three squats and specifically three bodyweight overhead squats at $t_3$, $t_5$, and $t_7$. It should be understood, however, that a different number of repetitions may be utilized and is within the teachings presented herein. That is, N iterations of movement is provided for by the teachings presented herein. At times $t_1$ and $t_9$, the user $U_2$ is at a neutral position, which may be detected by sensing the body point data within the virtual volumetric area 28 of the stage 24 or at $t_9$, an exercise end position which is sensed with the torso in an upright position superposed above the left leg and the right leg with the left arm and right arm laterally offset to the torso.

At times $t_2$, $t_4$, $t_6$, and $t_8$, the user $U_2$ is at an exercise start position. The exercise start position may be detected by the torso in an upright position superposed above the left leg and the right leg with the left arm and the right arm superposed above the torso. From an exercise start position, the user $U_2$ begins a squat with an exercise trigger. During the squat or other exercise movement, image frames are collected. The exercise trigger may be displacement of the user from the exercise start position by sensing displacement of the body. Each repetition of the exercise movement, such as a squat, may be detected by sensing the body returning to its position corresponding to the exercise start position. By way of example, the spine midpoint may be monitored to determine or mark the completion of exercise movement repetitions.

Figure 5:
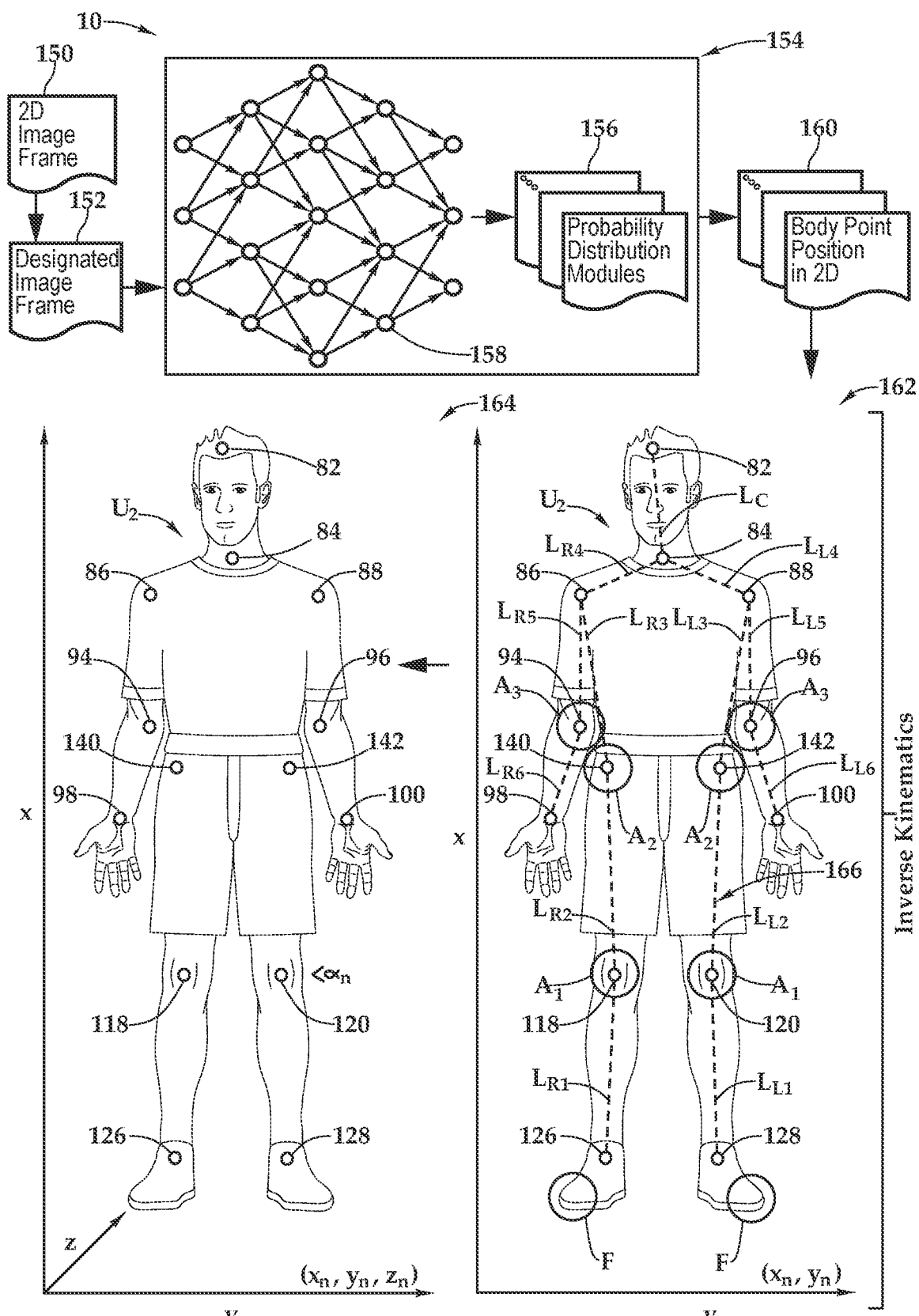
FIG. 5 is a diagram depicting one embodiment of an image frame processing by the system.

Referring to FIG. 5, by way of example, an image frame 150 is captured having data at a time $t_1$. The image frame 150 includes at each image element, coordinate values that are monoptic and represent two-dimensional coordinate values. Pre-processing occurs to the image frame 150 to provide a designated image frame format 152, which represents the pre-processing of the image frame 150. Such pre-processing includes isolation of an object, i.e., the user $U_2$. Next, as shown at a pose estimator 154, probability distribution models 156 generated by a neural network 158 are applied to the designated image frame format 152 to identify body parts, such as skeleton points, as shown by two-dimensional dataset 160.

The two-dimensional dataset 160 is then converted via an application of inverse kinematics 162 into a three-dimensional dataset 164 prior to the position of each of the respective body parts being determined within the three-dimensional dataset 164. More particularly, as shown, the two-dimensional dataset 160 includes various of the designated body part data 72, including the head data 82, the neck data 84, the right shoulder data 86, the left shoulder data 88, the right elbow data 94, the left elbow data 96, the right wrist data 98, the left wrist data 100, the right knee data 118, the left knee data 120, the right ankle data 126, the left ankle data 128, the right hip data 140, and the left hip data 142, for example. A horizontal axis (designated y) and a vertical axis (designated x) are defined in the two-dimensional dataset 160. An intersection is fixed at F between the two-dimensional dataset 160 and the horizontal axis (designated y) as a start of a kinematic chain 166. The intersection corresponds to feet of the user $U_2$.

Then, the smart device 12 calculates variable joint parameters under assumptions $A_1$, $A_2$, $A_3$, for example, that limb lengths $L_{L1}$, $L_{L2}$, $L_{L3}$, $L_{L4}$, $L_{L5}$, $L_{L6}$, $L_{R1}$, $L_{R2}$, $L_{R3}$, $L_{R4}$, $L_{R5}$, $L_{R6}$, have at least two hinge joints with a component of movement in a depth axis (designated z) perpendicular to the horizontal axis (designated y) and the vertical axis (designated x). In particular, the assumption $A_1$ relates to the knees, as represented by the right knee data 118 and the left knee data 120, having a component of movement in a depth axis (designated z); the assumption $A_2$ relates to the hips, as represented by the right hip data 140 and the left hip data 142, having a component of movement in a depth axis (designated z); and the assumption $A_3$ relates to the elbows, as represented by the right elbow data 94 and the left elbow data 96, having a component of movement in a depth axis (designated z).

The limb length $L_{L1}$ defines the length from the left ankle data 128 to the left knee data 120; the limb length $L_{L2}$ defines the length from the left knee data 120 to the left hip data 142; the limb length $L_{L3}$ defines the length from the left hip data 142 to the left shoulder data 88; the limb length $L_{L4}$ defines the length from the left shoulder data 88 to the neck data 84; the limb length $L_{L5}$ defines the length from the left shoulder data 88 to the left elbow data 96; and the limb length $L_{L6}$ defines the length from the left elbow data 96 to the left wrist data 100. Similarly, the limb lengths $L_{R1}$, $L_{R2}$, $L_{R3}$, $L_{R4}$, $L_{R5}$, $L_{R6}$ respectively relate to the segments the right ankle data 126 to the right knee data 118, the right knee data 118 to the right hip data 140, the right hip data 140 to the right shoulder data 86, the right shoulder data 86 to the neck data 84; the right shoulder data 86 to the right elbow data 94, and the right elbow data 94 to the right wrist data 98. The limb length $L_c$ relates to the length from the neck data 84 to the head data 82.

The smart device 12 also calculates variable joint parameters with respect to limb lengths of the user $U_2$ required to place the ends of the kinematic chain 166 in a given position and orientation relative to the start of the kinematic chain 166 at the fixed intersection F. The position of each of the body parts in the image frame 150, which were in two dimensions (e.g., $x_n$, $y_n$) is calculated with respect to the image frame 150 to provide three-dimensional coordinates (e.g. $x_n$, $y_n$, $z_n$) and provide joint positions, for example, such as angle alpha$_n$.

Figure 6:
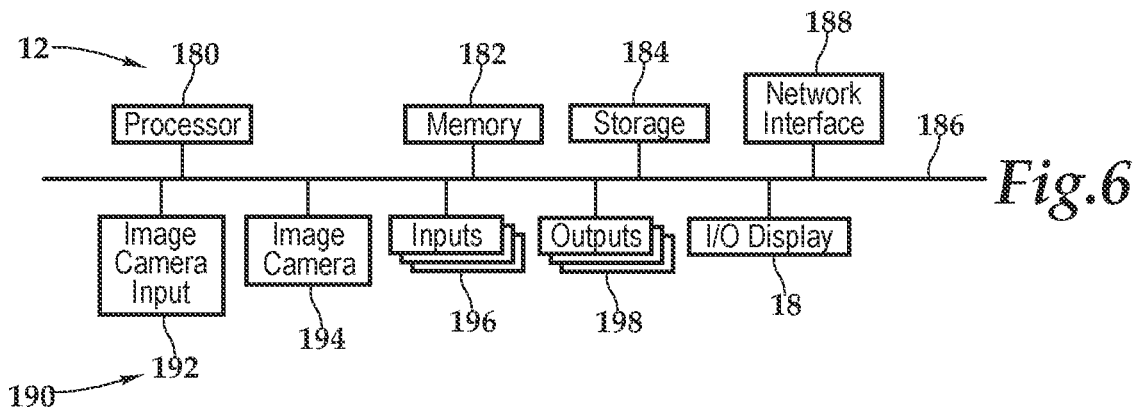
FIG. 6 is a functional block diagram depicting one embodiment of a smart device, which forms a component of the system presented in FIGS. 1A and 1B.

Referring to FIG. 6, within the housing 14 of the smart device 12, a processor 180, memory 182, and storage 184 are interconnected by a busing architecture 186 within a mounting architecture that also interconnects a network interface 188, a camera 190, including an image camera input 192 and/or image camera 194, inputs 196, outputs 198, and the display 18. The processor 180 may process instructions for execution within the smart device 12 as a computing device, including instructions stored in the memory 182 or in storage 184. The memory 182 stores information within the computing device. In one implementation, the memory 182 is a volatile memory unit or units. In another implementation, the memory 182 is a non-volatile memory unit or units. The storage 184 provides capacity that is capable of providing mass storage for the smart device 12. The network interface 188 may provide a point of interconnection, either wired or wireless, between the smart device 12 and a private or public network, such as the Internet. The various inputs 196 and outputs 198 provide connections to and from the computing device, wherein the inputs 196 are the signals or data received by the smart device 12, and the outputs 198 are the signals or data sent from the smart device 12. The display 18 may be an electronic device for the visual presentation of data and may, as shown in FIG. 6, be an input/output display providing touchscreen control. The camera 190 may be enabled by an image camera input 192 that may provide an input to the optical sensing instrument 16, which may be a camera, a point-cloud camera, a laser-scanning camera, an infrared sensor, an RGB camera, or a depth camera, for example, or the camera 190 may be an image camera 194 directly integrated into the smart device 12. By way of further example, the optical sensing instrument 16 may utilize technology such as time of flight, structured light, or stereo technology. By way of still further example, in instances where the optical sensing instrument 16 is a depth camera, an RGB camera, a color camera, a structured light camera, a time of flight camera, a passive stereo camera, or a combination thereof may be employed. Further, it should be appreciated that the optical sensing instrument 16 may include two or more optical sensing instruments; that is, more than one sensing instrument may be employed. As mentioned, the smart device 12 and the housing 14 may be a device selected from the group consisting of (with or without tripods) smart phones, smart watches, smart wearables, and tablet computers, for example.

The memory 182 and storage 184 are accessible to the processor 180 and include processor-executable instructions that, when executed, cause the processor 180 to execute a series of operations. In a first series of operations, the processor-executable instructions cause the processor 180 to display an invitation prompt on the interactive portal. The invitation prompt provides an invitation to the user to enter the stage prior to the processor-executable instructions causing the processor 180 to detect the user on the stage by sensing body point data within the virtual volumetric area 28. By way of example and not by way of limitation, the body point data may include first torso point data, second torso point data, first left arm point data, second left arm point data, first right arm point data, second right arm point data, first left leg point data, second left leg point data, first right leg point data, and second right leg point data, for example.

The processor-executable instructions cause the processor 180 to display the exercise movement prompt 30 on the interactive portal 20. The exercise movement prompt 30 provides instructions for the user to execute an exercise movement for a set number of repetitions with each repetition being complete when the user returns to an exercise start position. The processor 180 is caused by the processor-executable instructions to detect an exercise trigger. The exercise trigger may be displacement of the user from the exercise start position by sensing displacement of the related body point data. The processor-executable instructions also cause the processor 180 to display an exercise end prompt on the interactive portal 20. The exercise end prompt provides instructions for the user to stand in an exercise end position. Thereafter, the processor 180 is caused to detect the user standing in the exercise end position.

The processor-executable instructions cause the processor 180 to calculate one or more of several scores including calculating a mobility score by assessing angles using the body point data, calculating an activation score by assessing position within the body point data, calculating a posture score by assessing vertical differentials within the body point data, and calculating a symmetry score by assessing imbalances within the body point data. The processor-executable instructions may also cause the processor 180 to calculate a composite score based on one or more of the mobility score, the activation score, the posture score, or the symmetry score. The processor-executable instructions may also cause the processor 180 to determine an exercise recommendation based on one or more of the composite score, the mobility score, the activation score, the posture score, or the symmetry score.

In a second series of operations, the processor-executable instructions cause the processor 180 to capture an image frame from the optical sensing instrument 16. The image frame may include at each image element, two-dimensional coordinate values including a point related to a distance from the optical sensing instrument 16. Then the processor 180 may be caused to convert the image frame into a designated image frame format. The designated image frame format may include at each image element, coordinate values relative to the image frame. The processor executable instructions may cause the processor 180 to access, through a pose estimator, and apply multiple probability distribution models to the designated image frame format to identify a respective plurality of body parts. In acquiring the multiple probability distribution models, the probability distribution models may be generated by a neural network. Next, the processor 180 may be caused to calculate the position of each of the plurality of body parts in the designated image frame format and then calculate the position of each of the plurality of body parts in the image frame.

In a third series of operations, the processor-executable instructions cause the processor 180 to capture, via the optical sensing instrument, an image frame relative to a user in a line-of-sight with the optical sensing instrument. The image frame may include at each image element monoptic coordinate values. The processor 180 is then caused by the processor-executable instructions to convert the image frame into a designated image frame format prior to providing the designated image frame format to a pose estimator. The processor 180 is caused to receive a two-dimensional dataset from the pose estimator and convert, using inverse kinematics, the two-dimensional dataset into a three-dimensional dataset. The processor 180 then calculates, using the three-dimensional dataset, the position of each of the respective plurality of body parts in the image frame.

In a fourth series of operations, the processor-executable instructions cause the processor 180 to convert, using inverse kinematics, the two-dimensional dataset into a three-dimensional dataset by first defining a horizontal axis and a vertical axis in the two-dimensional dataset. The processor-executable instructions then cause the processor 180 to fix an intersection of the two-dimensional dataset and the horizontal axis as a start of a kinematic chain. The intersection may correspond to feet of the user. The processor 180 is then caused to calculate variable joint parameters under assumptions that the limb lengths have at least two hinge joints with a component of movement perpendicular to the horizontal axis and the vertical axis. Then the processor 180 calculates the variable joint parameters with respect to limb lengths of the user required to place ends of the kinematic chain in a given position and orientation relative to the start of the kinematic chain.

The processor-executable instructions presented hereinabove include, for example, instructions and data which cause a general purpose computer, special purpose computer, or special purpose processing device to perform a certain function or group of functions. Processor-executable instructions also include program modules that are executed by computers in stand-alone or network environments. Generally, program modules include routines, programs, components, data structures, objects, and the functions inherent in the design of special-purpose processors, or the like, that perform particular tasks or implement particular abstract data types. Processor-executable instructions, associated data structures, and program modules represent examples of the program code means for executing steps of the systems and methods disclosed herein. The particular sequence of such executable instructions or associated data structures represents examples of corresponding acts for implementing the functions described in such steps and variations in the combinations of processor-executable instructions and sequencing are within the teachings presented herein.

With respect to FIG. 6, in some embodiments, the system for human motion detection and tracking may be at least partially embodied as a programming interface configured to communicate with a smart device. Further, in some embodiments, the processor 180 and the memory 182 of the smart device 12 and a processor and memory of a server may cooperate to execute processor-executable instructions in a distributed manner. By way of example, in these embodiments, the server may be a local server co-located with the smart device 12, or the server may be located remotely to the smart device 12, or the server may be a cloud-based server.

Figure 7:
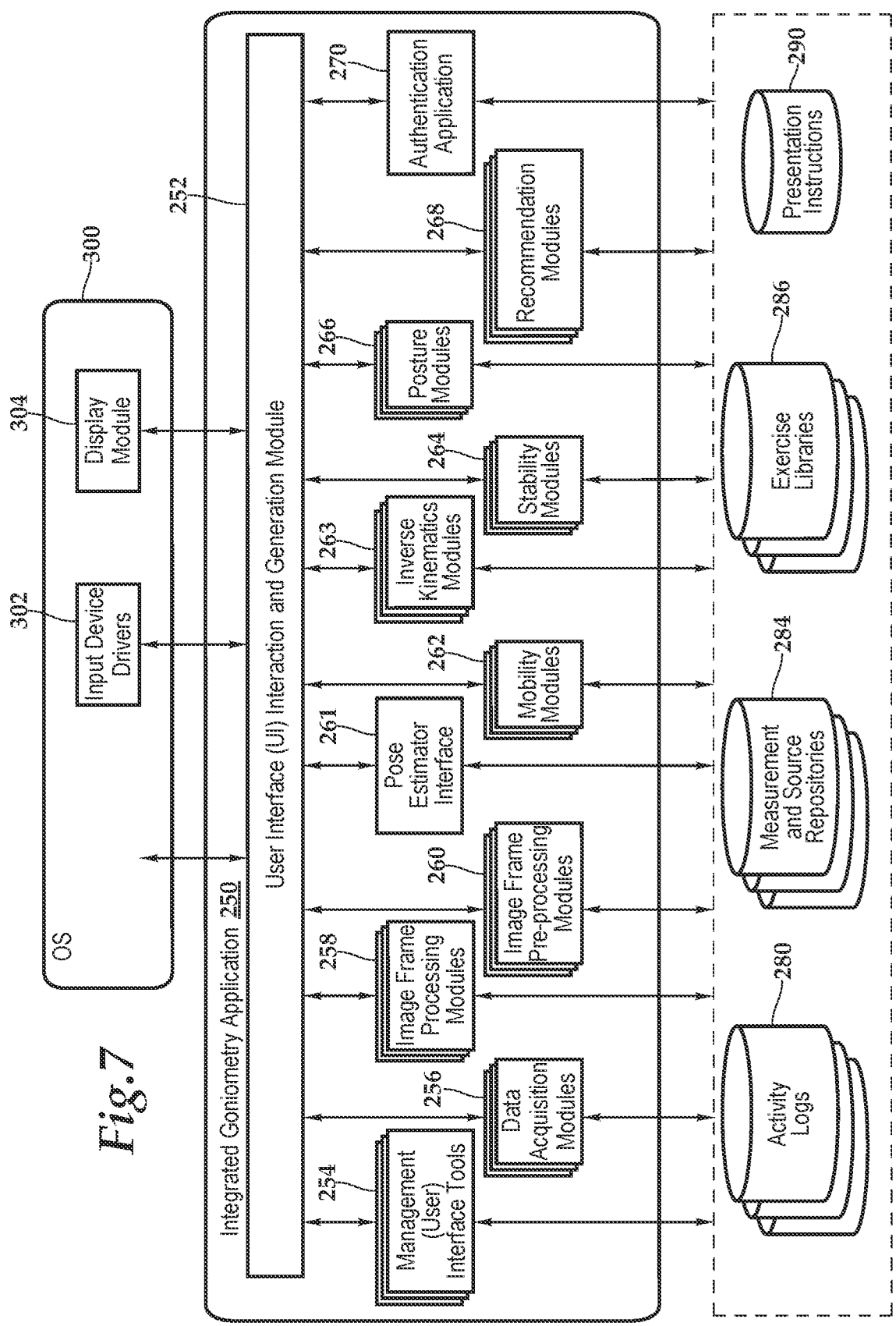
FIG. 7 is a conceptual module diagram depicting a software architecture of an integrated goniometry application of some embodiments.

FIG. 7 conceptually illustrates a software architecture of some embodiments of an integrated goniometry application 250 that may automate the biomechanical evaluation process and provide recommended exercises to improve physiological inefficiencies of a user. Such a software architecture may be embodied on an application installable on a smart device, for example. That is, in some embodiments, the integrated goniometry application 250 is a stand-alone application or is integrated into another application, while in other embodiments the application might be implemented within an operating system 300. In some embodiments, the integrated goniometry application 250 is provided on the smart device 12. Furthermore, in some other embodiments, the integrated goniometry application 250 is provided as part of a server-based solution or a cloud-based solution. In some such embodiments, the integrated goniometry application 250 is provided via a thin client. In particular, the integrated goniometry application 250 runs on a server while a user interacts with the application via a separate machine remote from the server. In other such embodiments, integrated goniometry application 250 is provided via a thick client. That is, the integrated goniometry application 250 is distributed from the server to the client machine and runs on the client machine.

The integrated goniometry application 250 includes a user interface (UI) interaction and generation module 252, management (user) interface tools 254, data acquisition modules 256, image frame processing modules 258, image frame pre-processing modules 260, a pose estimator interface 261, mobility modules 262, inverse kinematics modules 263, stability modules 264, posture modules 266, recommendation modules 268, and an authentication application 270. The integrated goniometry application 250 has access to activity logs 280, measurement and source repositories 284, exercise libraries 286, and presentation instructions 290, which presents instructions for the operation of the integrated goniometry application 250 and particularly, for example, the aforementioned interactive portal 20 on the display 18. In some embodiments, storages 280, 284, 286, and 290 are all stored in one physical storage. In other embodiments, the storages 280, 284, 286, and 290 are in separate physical storages, or one of the storages is in one physical storage while the other is in a different physical storage.

The UI interaction and generation module 250 generates a user interface that allows, through the use of prompts, the user to quickly and efficiently perform a set of exercise movements to be monitored, with the body point data collected from the monitoring furnishing an automated biomechanical movement assessment scoring and related recommended exercises to mitigate inefficiencies. Prior to the generation of automated biomechanical movement assessment scoring and related recommended exercises, the data acquisition modules 256 may be executed to obtain instances of the body point data via the optical sensing instrument 16, which is then processed with the assistance of the image frame processing modules 258 and the image frame pre-processing modules 260. The pose estimator interface 261 is utilized to provide, in one embodiment, image frame pre-processing files created by the image pre-processing modules 260 to a pose estimator to derive skeleton points and other body point data. Following the collection of the body point data, the inverse kinematics modules 263 derives three-dimensional data including joint position data. Then, the mobility modules 262, stability modules 264, and the posture modules 266 are utilized to determine a mobility score, an activation score, and a posture score, for example. More specifically, in one embodiment, the mobility modules 262 measure a user's ability to freely move a joint without resistance. The stability modules 264 provide an indication of whether a joint or muscle group may be stable or unstable. The posture modules 266 may provide an indication of physiological stresses presented during a natural standing position. Following the assessments and calculations by the mobility modules 262, stability modules 264, and the posture modules 266, the recommendation modules 268 may provide a composite score based on the mobility score, the activation score, and the posture score as well as exercise recommendations for the user. The authentication application 270 enables a user to maintain an account, including an activity log and data, with interactions therewith.

In the illustrated embodiment, FIG. 7 also includes the operating system 300 that includes input device drivers 302 and a display module 304. In some embodiments, as illustrated, the input device drivers 302 and display module 304 are part of the operating system 300 even when the integrated goniometry application 250 is an application separate from the operating system 300. The input device drivers 302 may include drivers for translating signals from a keyboard, a touch screen, or an optical sensing instrument, for example. A user interacts with one or more of these input devices, which send signals to their corresponding device driver. The device driver then translates the signals into user input data that is provided to the UI interaction and generation module 252.

Figure 8:
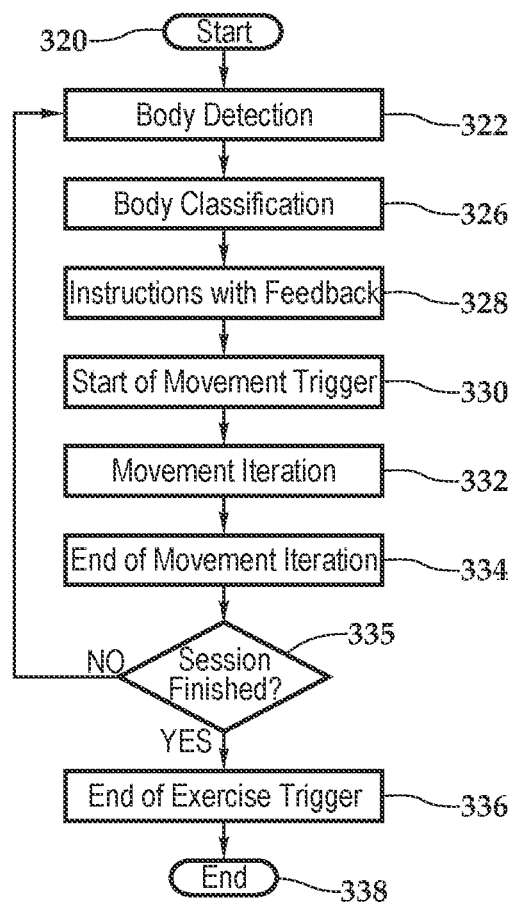
FIG. 8 is a flow chart depicting one embodiment of a method for integrated goniometric analysis according to exemplary aspects of the teachings presented herein.

FIG. 8 depicts one embodiment of a method for integrated goniometric analysis. At block 320, the methodology begins with the smart device positioned facing the stage. At block 322, multiple bodies are simultaneously detected by the smart device in and around the stage. As the multiple bodies are detected, a prompt displayed on the interactive portal of the smart device invites one of the individuals to the area of the stage in front of the smart device. At block 326, one of the multiple bodies is isolated by the smart device 12 and identified as an object of interest once it separates from the group of multiple bodies and enters the stage in front of the smart device 12. The identified body, a user, is tracked as a body of interest by the smart device.

At block 328, the user is prompted to position himself into the appropriate start position which will enable the collection of a baseline measurement and key movement measurements during exercise. At this point in the methodology, the user is prompted by the smart device to perform the exercise start position and begin a set repetitions of an exercise movement. The smart device collects body point data to record joint angles and positions. At block 330, the smart device detects an exercise or movement trigger which is indicative of phase movement discrimination being performed in a manner that is independent of the body height, width, size or shape of the user.

At block 332, the user is prompted by the smart device to repeat the exercise movement as repeated measurements provide more accurate and representative measurements. A repetition is complete when the body of the user returns to the exercise start position. The user is provided a prompt to indicate when the user has completed sufficient repetitions of the exercise movement. With each repetition, once in motion, monitoring of body movement will be interpreted to determine a maximum, minimum, and moving average for the direction of movement, range of motion, depth of movement, speed of movement, rate of change of movement, and change in the direction of movement, for example. At block 334, the repetitions of the exercise movement are complete. Continuing to decision block 335, if the session is complete, then methodology advances to block 336. If the session is not complete, then the methodology returns to the block 322. At block 336, once the required number of repetitions of the exercise movement are complete, the user is prompted to perform an exercise end position, which is a neutral pose. Ending at block 338, with the exercise movements complete, the integrated goniometry methodology begins calculating results and providing the results and any exercise recommendations to the user.

Figure 9:
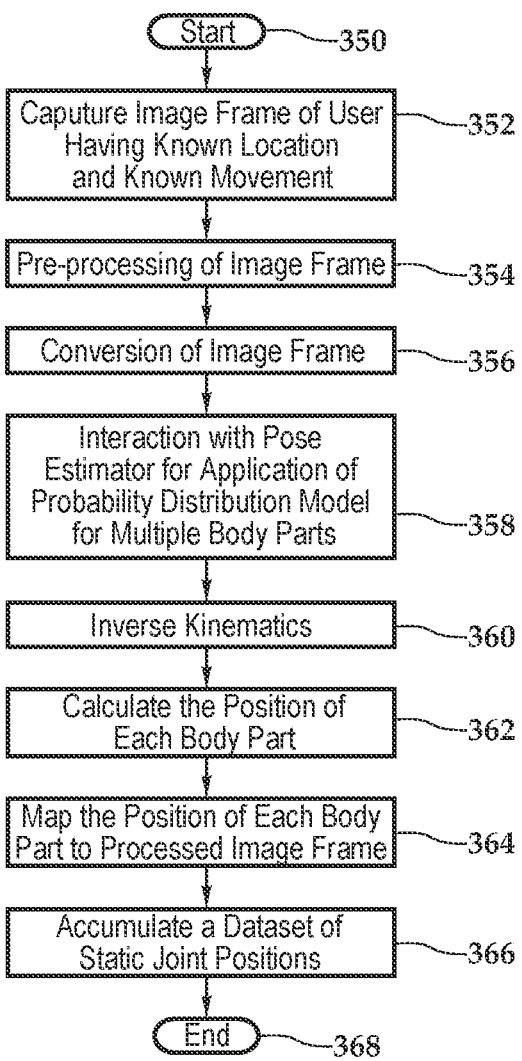
FIG. 9 is a flow chart depicting one embodiment of a method for human motion detection and tracking according to the teachings presented herein.
Figure 10:
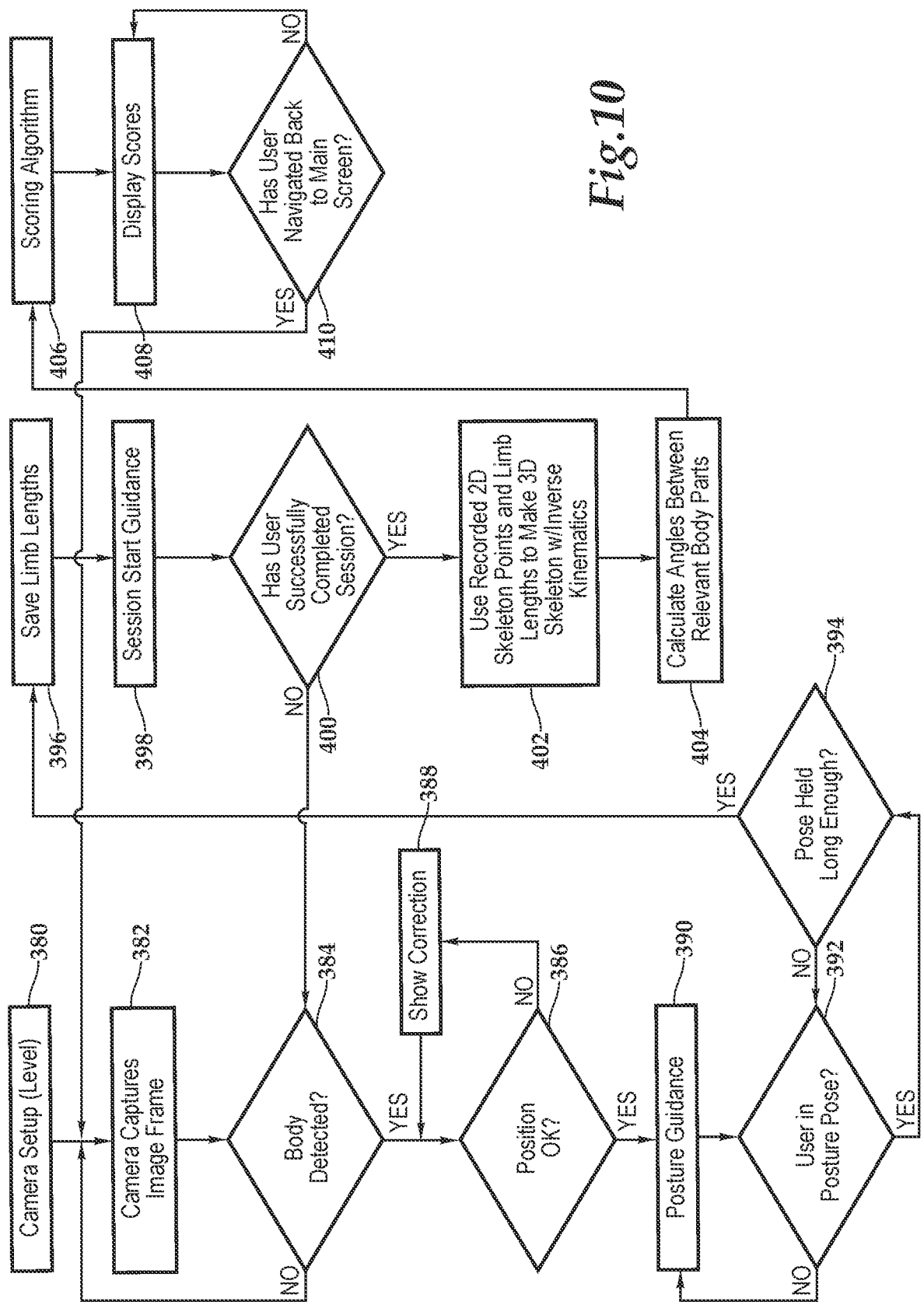
FIG. 10 is a flow chart depicting another embodiment of a method for human motion detection and tracking.

FIG. 9 and FIG. 10 show the methodology in more detail with elements 350 through 366 and elements 380 through 410. Referring now to FIG. 9, the methodology begins with block 350 and continues to block 352 where an image frame is captured. The image frame may be captured by the optical sensing instrument. By way of example and not by way of limitation, image frame acquisition may involve obtaining raw image frame data from the camera. Additionally, in some embodiments, the image frame is captured of a user at a known location performing a known movement, such as a squat. At block 354, pre-processing of the image frame occurs. As previously discussed, during pre-processing, the image frame is converted into a designated image frame format such that at each image element monoptic coordinate values are present relative to the image frame. Also, during the pre-processing, the object—the body of the user—may be isolated. At block 356, the image frame is converted into the designated image frame format before the submission at block 358 to a pose estimator for the application of a probability distribution model or models occurs for the body parts. Following the return of the data from the pose estimator, at block 360, inverse kinematics are applied to infer three-dimensional data, such as joint positions, from the two-dimensional data.

The three-dimensional dataset may include time-independent static joint positions. It is very common for applications using body pose estimation to be focused on time domain measurements, like attempting to gauge the speed or direction of a movement by comparing joint or limb positions across multiple video frames. Often the goal is to classify the observed movement, for instance using velocity or acceleration data to differentiate falling down from sitting down. In contrast, in some embodiments, the systems and methods presented herein focus on accumulating a dataset of static joint positions that can be used to accurately calculate relevant angles between body parts to assess a session of multiple overhead squats. In these embodiments, the systems and methods know in advance exactly where the user is located in the frame and what the movement will be. It is not necessary to use time domain data to identify the movement being performed or to estimate the speed at which it is performed.

In these embodiments, the assessment does not utilize any time domain data to analyze and score performance of the overhead squats. The only reason for use of the time domain data (i.e., across multiple video frames) may be to examine joint position changes in the time domain to determine when a user is no longer moving to inform a prompt to provide next step guidance. While the created dataset contains joint position data for a group of sequential video frames, the analysis of that data is strictly time-independent. The analysis of the joint position frame data for a squat would be the same no matter if the frames were analyzed in the order they were captured or in random order, since angles or scores are not calculated in the time domain. That is, the systems and methods presented herein calculate, using the three-dimensional dataset in a non-time domain manner, a position of each of a respective plurality of body parts in the image frame. The position of each of the body parts may be calculated more accurately at block 364 before the position of each body part is mapped at block 366 and the process concludes at block 368.

Referring now to FIG. 10, the methodology is initiated with the operation of the camera at block 380 to ensure the camera is level. At block 382, the camera captures an image frame, and the methodology detects a body at decision block 384. If a body is not detected, then the methodology returns to block 382. On the other hand, if a body is detected, then the position of the body is evaluated at decision block 386. If the position of the body has issues, such as the body not being completely in the frame or the body not being square with respect to the frame, then the methodology proceeds to block 388, where a correction is presented to assist the user with correcting the error before re-evaluation at decision block 386.

Once the position at decision block 386 is approved, then the methodology advances to posture guidance at block 390 before the posture is evaluated at decision block 392. If the posture of the user is correct, then the methodology advances to decision block 394. On the other hand if the user's pose does not present the correct posture, then the methodology returns to block 390 where posture guidance is provided. At decision block 394, if the pose is held long enough then the methodology advances to block 396 where limb length data is saved. If the pose is not held long enough, then the process returns to decision block 392.

At block 398, session guidance starts and the session, which presents exercises or poses for the user to complete, continues until completion unless, as shown at decision block 400, the session is interrupted or otherwise not completed. If the session is not completed, as shown by decision block 400, the methodology returns to decision block 384. At block 402 and block 404, the image frame is converted into the processed image frame and recorded two-dimensional skeleton points and limb lengths are utilized with inverse kinematics to calculate relevant angles between body parts. At block 406, the scoring algorithm is applied before scores are presented at block 408. At decision block 410, the scores will be continued to be displayed until the user navigates back to the main screen which returns the methodology to block 382.

The order of execution or performance of the methods and data flows illustrated and described herein is not essential, unless otherwise specified. That is, elements of the methods and data flows may be performed in any order, unless otherwise specified, and that the methods may include more or less elements than those disclosed herein. For example, it is contemplated that executing or performing a particular element before, contemporaneously with, or after another element are all possible sequences of execution.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. A system for human motion detection and tracking, the system comprising:
   a programming interface configured to communicate with a smart device, the smart device including a housing securing an optical sensing instrument, a processor, non-transitory memory, and storage therein, the smart device including a busing architecture communicatively interconnecting the optical sensing instrument, the processor, the non-transitory memory, and the storage; and the non-transitory memory accessible to the processor, the non-transitory memory including processor-executable instructions that, when executed by the processor, cause the system to:
  capture, via the optical sensing instrument, an image frame relative to a user in a line-of-sight with the optical sensing instrument, the image frame including at each image element monoptic coordinate values, the user being at a known location, the user performing a known movement,
  convert the image frame into a designated image frame format,
  provide the designated image frame format to a pose estimator,
  receive a two-dimensional dataset from the pose estimator,
  convert, using inverse kinematics, the two-dimensional dataset into a three-dimensional dataset, the three-dimensional dataset including a time-independent plurality of static joint positions, and
  calculate, using the three-dimensional dataset in a non-time domain manner, a position of each of a respective plurality of body parts in the image frame.

2. The system as recited in claim 1, wherein the processor-executable instructions to convert, using inverse kinematics, the two-dimensional dataset into the three-dimensional dataset further comprise processor-executable instructions that, when executed by the processor, cause the system to:
  define a horizontal axis and a vertical axis in the two-dimensional dataset,
  fix an intersection of the two-dimensional dataset and the horizontal axis as a start of a kinematic chain, and
  calculate variable joint parameters required to place ends of the kinematic chain in a given position and orientation relative to the start of the kinematic chain.

3. The system as recited in claim 1, wherein the processor-executable instructions to convert, using inverse kinematics, the two-dimensional dataset into the three-dimensional dataset further comprise processor-executable instructions that, when executed by the processor, cause the system to:
  define a horizontal axis and a vertical axis in the two-dimensional dataset,
  fix an intersection of the two-dimensional dataset and the horizontal axis as a start of a kinematic chain, the intersection corresponding to feet of the user, and
  calculate variable joint parameters with respect to limb lengths of the user required to place ends of the kinematic chain in a given position and orientation relative to the start of the kinematic chain.

4. The system as recited in claim 1, wherein the processor-executable instructions to convert, using inverse kinematics, the two-dimensional dataset into the three-dimensional dataset further comprise processor-executable instructions that, when executed by the processor, cause the system to:
  define a horizontal axis and a vertical axis in the two-dimensional dataset,
  fix an intersection of the two-dimensional dataset and the horizontal axis as a start of a kinematic chain, the intersection corresponding to feet of the user,
  calculate variable joint parameters under assumptions that limb lengths of the user have at least two hinge joints with a component of movement perpendicular to the horizontal axis and the vertical axis, and
  calculate the variable joint parameters with respect to the limb lengths of the user required to place ends of the kinematic chain in a given position and orientation relative to the start of the kinematic chain.

5. The system as recited in claim 4, wherein the at least two hinge joints comprise joints selected from the group consisting of knees, hips, and elbows.

6. The system as recited in claim 1, wherein the pose estimator further comprises a neural network.

7. The system as recited in claim 1, wherein the pose estimator further comprises a plurality of probability distribution models for the designated image frame format.

8. The system as recited in claim 1, wherein the optical sensing instrument further comprises an instrument selected from the group consisting of a camera, a point-cloud camera, a laser-scanning camera, an infrared sensor, and an RGB camera.

9. The system as recited in claim 1, wherein the optical sensing instrument further comprises a technology selected from the group consisting of time of flight, structured light, and stereo technology.

10. The system as recited in claim 1, wherein the optical sensing instrument further comprises a depth camera.

11. The system as recited in claim 10, wherein the depth camera further comprises a camera selected from the group consisting of a structured light camera, a color camera, a time of flight camera, a passive stereo camera, and combinations thereof.

12. The system as recited in claim 1, wherein the optical sensing instrument further comprises a plurality of cameras.

13. The system as recited in claim 1, wherein the housing of the smart device further comprises a display communicatively interconnected with the busing architecture.

14. The system as recited in claim 13, wherein the memory further comprises processor-executable instructions that, when executed, cause the processor to display on an instruction prompt on an interactive portal of the display, the instruction prompt providing instructions for the user.

15. The system as recited in claim 14, wherein the memory further comprises processor-executable instructions that, when executed, cause the processor to:
  detect the user in a baseline position,
  display an exercise prepare prompt on the interactive portal, the exercise prepare prompt providing instructions for the user to stand in an exercise start position,
  detect the user in the exercise start position,
  display an exercise movement prompt on the interactive portal, the exercise movement prompt providing instructions for the user to execute an exercise movement for a set number of repetitions, each repetition being complete when the user returns to the exercise start position, and
  detect an exercise trigger, the exercise trigger being displacement of the user from the exercise start position by sensing displacement.

16. The system as recited in claim 1, wherein the smart device further comprises a device selected from the group consisting of smart phones, smart watches, smart wearables, and tablet computers.

17. The system as recited in claim 1, wherein the monoptic coordinate values further comprise two-dimensional coordinate values.

18. A system for human motion detection and tracking, the system comprising:
  a programming interface configured to communicate with a smart device, the smart device including a housing securing an optical sensing instrument, a processor, non-transitory memory, and storage therein, the smart device including a busing architecture communicatively interconnecting the optical sensing instrument, the processor, the non-transitory memory, and the storage;

the non-transitory memory accessible to the processor, the non-transitory memory including first processor-executable instructions that, when executed by the processor, cause the system to:

capture, via the optical sensing instrument, an image frame relative to a user in a line-of-sight with the optical sensing instrument, the image frame including at each image element monoptic coordinate values, the user being at a known location, the user performing a known movement, convert the image frame into a designated image frame format, provide the designated image frame format to a pose estimator, receive a two-dimensional dataset from the pose estimator, convert, using inverse kinematics, the two-dimensional dataset into a three-dimensional dataset, the three-dimensional dataset including a time-independent plurality of static joint positions, and calculate, using the three-dimensional dataset, the position of each of the respective plurality of body parts in the image frame; and the non-transitory memory accessible to the processor, the non-transitory memory including second processor-executable instructions that, when executed by the processor, cause the system to:

define a horizontal axis and a vertical axis in the two-dimensional dataset, fix an intersection of the two-dimensional dataset and the horizontal axis as a start of a kinematic chain, and calculate variable joint parameters required to place ends of the kinematic chain in a given position and orientation relative to the start of the kinematic chain.

19. The system as recited in claim 18, wherein the optical sensing instrument further comprises an instrument selected from the group consisting of a camera, a point-cloud camera, a laser-scanning camera, an infrared sensor, and an RGB camera.

20. A system for human motion detection and tracking, the system comprising:

a programming interface configured to communicate with a smart device, the smart device including a housing securing an optical sensing instrument, a processor, non-transitory memory, and storage therein, the smart device including a busing architecture communicatively interconnecting the optical sensing instrument, the processor, the non-transitory memory, and the storage;

the non-transitory memory accessible to the processor, the non-transitory memory including first processor-executable instructions that, when executed by the processor, cause the system to:

capture, via the optical sensing instrument, an image frame relative to a user in a line-of-sight with the optical sensing instrument, the image frame including at each image element monoptic coordinate values, the user being at a known location, the user performing a known movement, convert the image frame into a designated image frame format, provide the designated image frame format to a pose estimator, the pose estimator having a plurality of probability distribution models for the designated image frame format, receive a two-dimensional dataset from the pose estimator, convert, using inverse kinematics, the two-dimensional dataset into a three-dimensional dataset, the three-dimensional dataset including a time-independent plurality of static joint positions, and calculate, using the three-dimensional dataset, the position of each of the respective plurality of body parts in the image frame; and the non-transitory memory accessible to the processor, the non-transitory memory including second processor-executable instructions relative to the inverse kinematics that, when executed by the processor, cause the system to:

define a horizontal axis and a vertical axis in the two-dimensional dataset, fix an intersection of the two-dimensional dataset and the horizontal axis as a start of a kinematic chain, and calculate variable joint parameters required to place ends of the kinematic chain in a given position and orientation relative to the start of the kinematic chain.

\* \* \* \* \*